(12) United States Patent
Babaev

(10) Patent No.: US 7,943,352 B2
(45) Date of Patent: May 17, 2011

(54) APPARATUS AND METHODS FOR VACCINE DEVELOPMENT USING ULTRASOUND TECHNOLOGY

(75) Inventor: Eilaz P. Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 841 days.

(21) Appl. No.: 11/393,180

(22) Filed: Mar. 29, 2006

(65) Prior Publication Data

US 2007/0231346 A1    Oct. 4, 2007

(51) Int. Cl.
    *C12N 13/00* (2006.01)
(52) U.S. Cl. .................................. 435/173.1; 435/173.7
(58) Field of Classification Search ............... 435/173.1, 435/173.7
    See application file for complete search history.

(56) References Cited

U.S. PATENT DOCUMENTS

| | | | |
|---|---|---|---|
| 3,137,629 A | 6/1964 | Cocking et al. | |
| 3,933,592 A | 1/1976 | Clendenning | |
| 4,298,597 A | 11/1981 | Acres et al. | |
| 4,837,018 A | 6/1989 | Konishi et al. | |
| 5,074,474 A * | 12/1991 | Golz et al. .......................... | 241/1 |
| 5,076,266 A | 12/1991 | Babaev | |
| 5,582,829 A | 12/1996 | Alliger et al. | |
| 5,597,572 A | 1/1997 | Huergo et al. | |
| 5,611,993 A | 3/1997 | Babaev | |
| 5,688,682 A | 11/1997 | Mulks et al. | |
| 5,747,653 A | 5/1998 | Huergo et al. | |
| 6,022,728 A | 2/2000 | Mulks et al. | |
| 6,071,480 A * | 6/2000 | Halaka ............................ | 422/128 |
| 6,303,129 B1 | 10/2001 | Alliger et al. | |
| 6,478,754 B1 | 11/2002 | Babaev | |
| 6,533,803 B2 | 3/2003 | Babaev | |
| 6,569,099 B1 | 5/2003 | Babaev | |
| 6,601,581 B1 | 8/2003 | Babaev | |
| 6,623,444 B2 | 9/2003 | Babaev | |
| 6,663,554 B2 | 12/2003 | Babaev | |
| 6,686,195 B1 * | 2/2004 | Colin et al. ................. | 435/306.1 |
| 6,723,064 B2 | 4/2004 | Babaev | |
| 6,761,729 B2 | 7/2004 | Babaev | |
| 6,960,173 B2 | 11/2005 | Babaev | |
| 6,964,647 B1 | 11/2005 | Babaev | |
| 2002/0082666 A1 | 6/2002 | Babaev | |
| 2002/0103448 A1 | 8/2002 | Babaev | |
| 2002/0138036 A1 | 9/2002 | Babaev | |
| 2002/0156400 A1 | 10/2002 | Babaev | |
| 2002/0190136 A1 | 12/2002 | Babaev | |
| 2003/0153961 A1 | 8/2003 | Babaev | |
| 2003/0171701 A1 | 9/2003 | Babaev | |
| 2003/0229304 A1 | 12/2003 | Babaev | |
| 2003/0236560 A1 | 12/2003 | Babaev | |
| 2004/0030254 A1 | 2/2004 | Babaev | |
| 2004/0186384 A1 | 9/2004 | Babaev | |
| 2005/0015024 A1 | 1/2005 | Babaev | |
| 2005/0112135 A1 | 5/2005 | Cormier et al. | |
| 2006/0025716 A1 | 2/2006 | Babaev | |
| 2006/0058710 A1 | 3/2006 | Babaev | |
| 2007/0016110 A1 | 1/2007 | Babaev | |
| 2007/0031611 A1 | 2/2007 | Babaev | |
| 2007/0051307 A1 | 3/2007 | Babaev | |
| 2007/0088217 A1 | 4/2007 | Babaev | |
| 2007/0088245 A1 | 4/2007 | Babaev | |
| 2007/0088386 A1 | 4/2007 | Babaev | |
| 2007/0185527 A1 | 8/2007 | Babaev | |
| 2007/0231346 A1 | 10/2007 | Babaev | |
| 2007/0233054 A1 | 10/2007 | Babaev | |
| 2007/0239250 A1 | 10/2007 | Babaev | |
| 2007/0244528 A1 | 10/2007 | Babaev | |

FOREIGN PATENT DOCUMENTS

| | | |
|---|---|---|
| EP | 424532 A4 | 12/1991 |
| EP | 416106 A4 | 3/1992 |
| EP | 1370321 A1 | 12/2003 |
| EP | 1322275 A4 | 10/2004 |
| EP | 1526825 A1 | 5/2005 |
| EP | 1596940 A1 | 11/2005 |
| EP | 1617910 A1 | 1/2006 |
| EP | 1355696 A4 | 5/2006 |
| WO | WO 8600019 A1 * | 1/1986 |
| WO | 9011135 A1 | 10/1990 |
| WO | WO 9011088 A1 * | 10/1990 |
| WO | 9012655 A1 | 11/1990 |
| WO | 9707830 A1 | 3/1997 |
| WO | 9717933 A1 | 5/1997 |
| WO | 0224150 A3 | 3/2002 |
| WO | 02055131 A3 | 7/2002 |
| WO | 02055150 A3 | 7/2002 |
| WO | 02060525 A3 | 8/2002 |
| WO | 02028350 C1 | 10/2002 |
| WO | 02076547 A1 | 10/2002 |
| WO | 02085456 A1 | 10/2002 |
| WO | 2004014284 B1 | 7/2004 |
| WO | 2004089469 A1 | 10/2004 |
| WO | 2004091722 C1 | 10/2004 |
| WO | 2007002598 A3 | 1/2007 |
| WO | 2007018980 A3 | 2/2007 |

(Continued)

*Primary Examiner* — Allison M. Ford
*Assistant Examiner* — Susan E. Fernandez

(57) ABSTRACT

Method and device for the creation of vaccines using ultrasonic waves, comprised of an ultrasound generator and a transducer to produce ultrasonic waves, is disclosed. The transducer has a specific ultrasound tip depending upon the type of delivery method utilized and depending on the shape of the vial containing the solution of the virus, bacterium, or other infectious agent. The apparatus delivers ultrasonic waves to solution either directly through the insertion of the ultrasound tip into the solution, through a coupling medium adjacent to the vial or near the vial, or through an air or gas medium. The ultrasound waves have the effect of destroying the viable virus, bacterium, or other infectious agent and of releasing the appropriate antigens, thus resulting in a vaccine for that virus, bacterium, or other infectious agent.

17 Claims, 2 Drawing Sheets

FOREIGN PATENT DOCUMENTS

| | | | |
|---|---|---|---|
| WO | 2007021427 | A3 | 2/2007 |
| WO | 07046989 | A3 | 4/2007 |
| WO | 2007046990 | A2 | 4/2007 |
| WO | 2007117800 | A2 | 10/2007 |
| WO | 2007117964 | A2 | 10/2007 |
| WO | 2007121123 | A2 | 10/2007 |

* cited by examiner

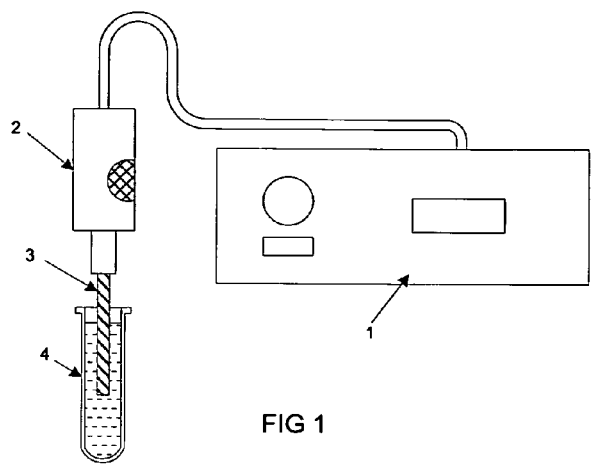 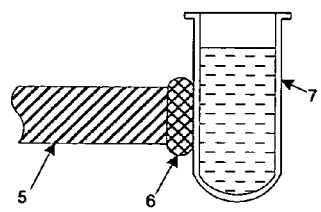 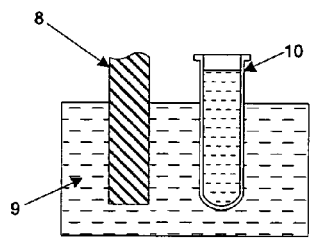 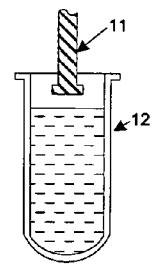 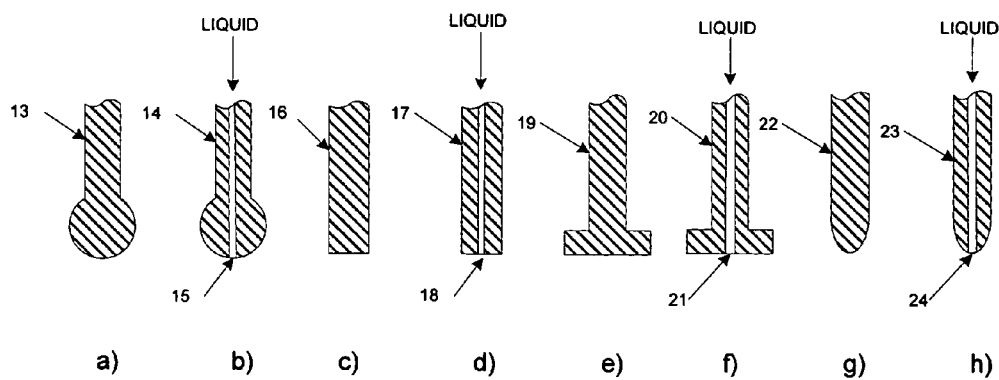

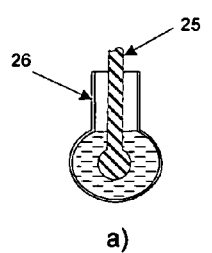 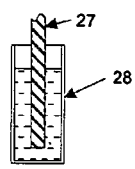 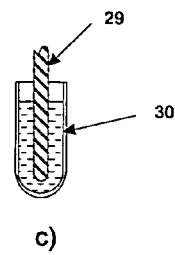 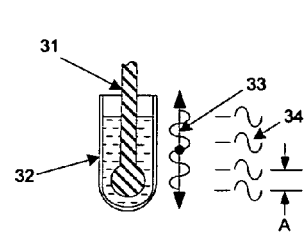
a)     b)     c)
FIG 6          FIG 7
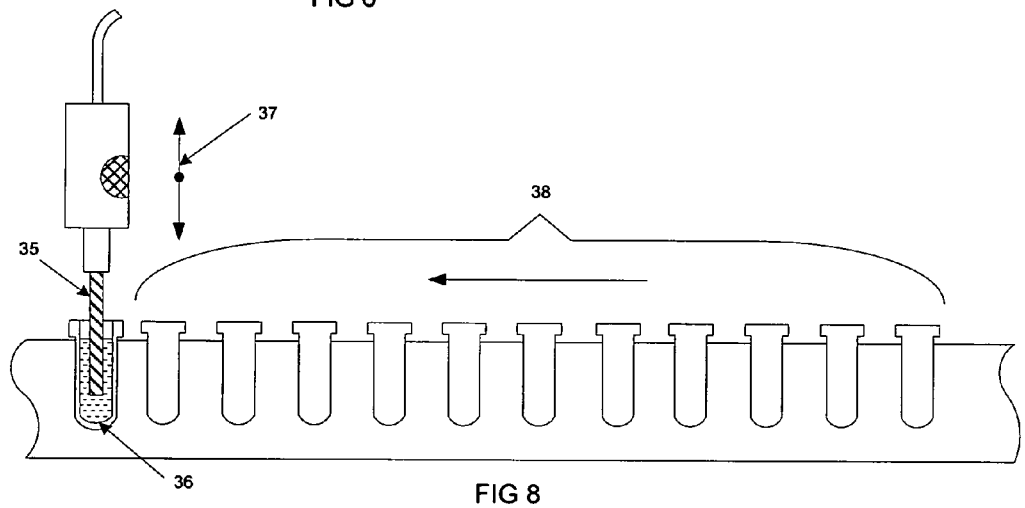
FIG 8
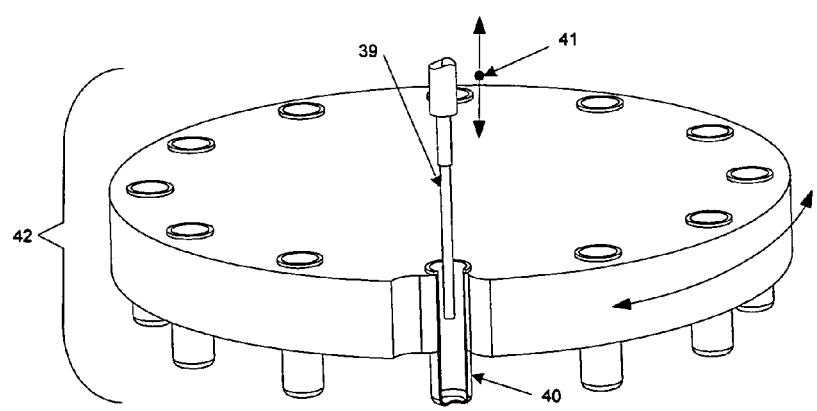
FIG 9

APPARATUS AND METHODS FOR VACCINE DEVELOPMENT USING ULTRASOUND TECHNOLOGY

BACKGROUND OF THE INVENTION

The present invention relates to the development of vaccines. In particular, the present invention relates to apparatus and methods for developing vaccines using ultrasound technology.

Vaccine research and development has seen an increased level of activity, especially with the recent development of biodefense initiatives. The process of recombinant genetic engineering has provided a potential new approach to creating new and improved vaccines for the treatment of disease. So far, this approach has met with limited success for a variety of reasons, and thus many vaccines are still produced via traditional methodologies.

Most classical vaccines are produced by one of two production methods that create either an inactivated (killed) or attenuated (live) vaccine product.

Inactivated vaccines (flu, cholera, hepatitis A) are produced by killing the disease causing microorganism. A number of different methods of inactivation can be used, including chemicals, irradiation, or heat. These vaccines are considered stable and relatively safe since they cannot revert to the virulent (disease-causing) form. The products often do not require refrigeration, a quality that makes them accessible and desirable to domestic healthcare personnel as well as those in developing countries because they are practical for vaccinating people who are in remote locations or involved in highly mobile activities (such as members of the armed force). However, most inactivated vaccines produce a relatively weak immune response and must be given more than once. A vaccine that requires multiple doses (boosters) may have a limited usefulness, especially in areas where people have limited access to regular healthcare.

The second classical approach to the production of vaccines is an attenuated or live vaccine (measles, mumps, rubella). The disease-causing organism is grown under special laboratory conditions that cause it to loose its virulence or disease causing properties. Products prepared in this way require special handling and storage in order to maintain their potency. These products produce both anti-body mediated and cell-mediated immunity and generally they will only require one booster dose.

While live vaccines do have some higher immune response advantages, this method of production has one large drawback. Because the organisms are still living, it is their nature to change or mutate, causing these products to have a remote possibility that the organisms may revert to a virulent form and potentially cause disease; thus, infection may occur either as a result of exposure while handling/processing the vaccine or after administration of the vaccine. Therefore, these vaccines must be carefully tested and monitored. Patients who have compromised immune systems are not usually administered live vaccines.

These two classical approaches to vaccine development and production not only make up the majority of vaccines in use today, but these approaches continue to be used in current vaccine development programs, including the development of vaccines for HIV/AIDS, newly identified variant strains of Hepatitis, etc.

Alliger previously discussed using ultrasound technology to create vaccines in U.S. Pats. Nos. 5,582,829 (Alliger) and 6,303,129 (Alliger). Alliger treats substantially viable cells, bacteria or viruses (i.e. those that are intact and capable of functioning) with ultrasound in order to make available antigens capable of inducing an immunogenic and/or therapeutic response. Specifically, the treatment of cells and viruses with ultrasound is intended to deactivate the potentially harmful cells and viruses and to also disperse the antigens present for use as a vaccine without further processing.

Alliger recommends that the procedure is conducted at room temperature while maintaining the temperature of the sample containing the microbe against which a vaccine is developed between zero and 5 degrees Celsius. The minimization of heat is to prevent the denaturing of the antigens. Denaturing these antigens would limit their ability to produce a specific immune response, thus diminishing the potential immunogenic effect of the vaccine. The Alliger method is to deliver ultrasound at a specific frequency, intensity, and duration in order to rupture and destroy the viruses and bacteria within the sample through cavitation, to disperse the available antigens, and to do so without raising the temperature of the viruses or bacteria to a level that would denature the antigens.

Alliger further states that the time must be sufficient to disrupt the viruses or cells so that no virulent cell structure remains to do this, Alliger states that one gram of cultured cells may generally require about 3 minutes of sonication.

As for sonicating the viruses and cells, Alliger delivered ultrasonic waves to the microbe sample through a liquid medium at a frequency of about 20 kHz to about 40 kHz. He stated that above this frequency range cavitation intensity is reduced considerably, even at high power inputs, so that cells or viruses may not be fully disintegrated. Alliger specifically stated that the minimum intensity of the sonic waves should be about 1 watt/sq. cm, and that the preferable intensity level at about 20 kHz is 50 to 175 watts/sq. cm.

Alliger failed to mention the role of using different ultrasound parameters and additional factors such as the volume of the sample/solution containing microorganisms and the geometrical shape of the ultrasound tip and vial/container to be used to achieve the most efficient results in ultrasonic vaccine development. Because of the shortcomings of the classical approaches and Alliger's approach, there is still a need for apparatus and methods that can produce inactivated vaccines that can both produce a stronger immune response and that can produce attenuated microorganisms for vaccine development incapable of reverting back to a virulent strain.

SUMMARY OF THE INVENTION

The present invention is directed towards improvements of apparatuses and methods for the creation of vaccines using ultrasound waves previously researched and tested by the author of this patent in the 1980's. Apparatus and methods in accordance with the present invention may meet the above-mentioned needs and also provide additional advantages and improvements that will be recognized by those skilled in the art upon review of the present disclosure.

The present invention comprises an ultrasonic generator, an ultrasonic transducer, a sonication tip, and a vial or container of a solution that can be sonicated to create vaccines. The solution contained in the vials is a mass of viruses, bacteria, or other infectious agents. The solution is sonicated with ultrasound waves to destroy the viable infectious virus, bacteria, or infectious agent while also releasing the appropriate antigens, thus resulting in a vaccine for that virus, bacterium, or other infectious agent.

Ultrasound waves can be delivered to the solution either directly through the insertion of the ultrasound tip into the solution, through a coupling medium, or through an air/gas medium. The ultrasound tip that is used can vary depending upon the type of delivery method chosen. There are three different types of recommended methods for sonicating a solution by the insertion of the ultrasound tip into the solution itself. The first method uses a special shaped vial where the ultrasound tip remains in the same position during the delivery of the ultrasound energy while the last two methods utilize movement of the ultrasound tip during the sonication treatment.

There are also different types of recommended methods for sonicating the solution through a coupling medium. There can be a medium placed between the tip and the vial, there can be a liquid medium through which to deliver ultrasound waves, or the vial/container itself can be used as a medium if the tips is pressed up against the vial/container.

Based on the ultrasound intensity that is utilized, the sonication time of the solution can vary. However, the intensity of the ultrasound waves can be controlled through a variation in the ultrasound parameters such as the frequency, the amplitude and the treatment time. The process may require different intensity levels and ultrasound parameters based on the specific type of virus, bacterium or other infectious agent used to create the vaccine and based on the volume of the solution containing microbes to be sonicated.

The invention is related to the apparatus and methods of delivering ultrasound energy to viruses, bacteria, or other infectious agents in order to create a vaccine to treat the virus, bacterium, or infectious agent.

One aspect of this invention may be to provide a method and device for the creation of different vaccines.

Another aspect of the invention may be to provide a method and device for the creation of vaccines without the risk of toxicity that occurs with other chemical and temperature creation methods.

Another aspect of the invention may be to provide a method and device for the creation of high quality vaccines.

Another aspect of the invention may be to provide a method and device for the improvement of vaccine creation methods without using temperature or chemical influences.

Another aspect of the invention may be to provide a method and device for the creation of vaccines with a decreased production time.

Another aspect of the invention may be to provide a method and device for the continuous production of vaccines.

Another aspect of the invention may be to provide a method and device for the mass production of vaccines.

These and other aspects of the invention will become more apparent from the written descriptions and figures below.

BRIEF DESCRIPTION OF THE DRAWINGS

The present invention will be shown and described with reference to the drawings of preferred embodiments and clearly understood in details.

FIG. 1 is a perspective view of an ultrasound vaccine development system where the ultrasound tip is inserted into the solution.

FIG. 2 is a cross-sectional view of an ultrasound tip connected via a coupling medium to a vial.

FIG. 3 is a cross-sectional view of an ultrasound tip inserted into a liquid bath with a vial also inserted into the bath to deliver ultrasound energy through the liquid to the vial.

FIG. 4 is a cross-sectional view of an ultrasound tip inserted into a vial but located at a distance from the solution in the vial.

FIG. 5 are cross-sectional views of example ultrasound tips for use in the ultrasound vaccine development system.

FIG. 6 are cross-sectional views of example different shaped vials for use in the ultrasonic vaccine development system where the tip is inserted directly into the solution and sonicates the solution from a constant position.

FIG. 7 is a cross-sectional view of recommended sonication methods to use with the ultrasound vaccine development system where the tip is inserted into the solution and moves during sonication.

FIG. 8 is a cross-sectional view of a production-line method to use with the ultrasound vaccine development system.

FIG. 9 is a cross-sectional view of a carousel method to use with the ultrasound vaccine development system.

DETAILED DESCRIPTION OF THE INVENTION

The present invention is an apparatus and methods for the development of vaccines using ultrasound technology. Preferred embodiments of the present invention in the context of an apparatus and methods are illustrated in the figures and described in detail below.

FIG. 1 illustrates the vaccine creation apparatus that has an ultrasonic generator 1, an ultrasonic transducer 2, a sonication tip 3, and a vial 4 or other container in which a solution will be placed. The solution in the vial or container is a mass of viruses, bacteria, or other infectious agents. The solution is sonicated with ultrasound waves to destroy the viable infectious virus, bacterium, or other infectious agent while also releasing the appropriate antigens, thus resulting in a vaccine against that virus, bacterium, or other infectious agent. Because the resulting vaccine is available for immediate use, the production time of vaccines developed through this method is lower than the production time of vaccines developed through classical methods mentioned above. Ultrasound waves can be delivered to solution either directly through the insertion of the ultrasound tip into the solution FIG. 1, through a coupling medium adjacent to the vial FIG. 2 or near the vial FIG. 3, or through the air or gas medium FIG. 4.

FIG. 5 shows examples of recommended ultrasound tips that can be used depending on the type of delivery method. FIG. 5a is a spherical ultrasound tip 13 and FIG. 5b is a spherical ultrasound tip 14 that contains a central orifice 15. FIGS. 5c/5d/5e/5f show ultrasound tips with a flat radiation surface. FIGS. 5c and 5e are ultrasound tips 16 and 17 with a flat radiation surface, and FIGS. 5d and 5f are ultrasound tips 17 and 20 with flat radiation surfaces and central orifices 18 and 21. FIGS. 5g and 5h show ultrasound tips 22 and 23 with a curved radiation surface. FIG. 5e shows an ultrasound tip 23 with a curved radiation surface and a central orifice 24. The central orifices of the ultrasound tips shown in FIG. 5 can be used to deliver solution into a vial or container and/or can be used to provide sonication during or after delivery of the solution.

FIG. 1 shows direct sonication where the ultrasound tip 3 is inserted into the vial 4 and into the solution—the recommend tip 3 to use is either a sphere FIGS. 5a/5b, a flat radiation surface FIGS. 5c/5d/5e/5f, a rectangular prism (not shown), or another similar shape or combination of shapes, with the sphere FIGS. 5a/5b as the preferred tip. The most preferred tip is the spherical tip 14 that contains a central orifice 15; this is because the most preferred treatment method involves the use of a spherical sonication tip where the solution is delivered into the vial or container through the central orifice.

FIG. 2 shows delivery of ultrasound energy from an ultrasound tip 5 through a coupling medium 6 such as liquid, gel, or the glass/plastic vial 7, where the tip 5 is pressed up against the vial 7 or container—the recommended configuration of tip 5 is one that matches the shape of tip 5 to the geometric shape of the vial 7 or container. For example, if a spherical vial is to be sonicated, the recommend tip would be a curved-shape tip (not shown) so that the tip would fit around the shape of the vial.

FIG. 3 shows delivery of ultrasound energy from an ultrasound tip 8 through a liquid medium 9 where the ultrasound tip 8 is located at a distance from the vial 10—the recommended tip to use is a flat shaped tip FIG. 5c/FIG. 5d, with the preferred tip being a flat shaped tip without a central office as depicted in FIG. 5c. For this method, the ultrasound tip 8 is placed into the liquid medium 9 and delivers ultrasound energy to the vial 10 through the liquid medium 9.

FIG. 4 shows delivery of ultrasound energy from an ultrasound tip 11 to a vial 12 through an air or gas medium—the recommended tip to use is a flat-shaped tip FIGS. 5c/5d/5e/5f, with the preferred tip either FIG. 5c or 5e. For this delivery method, the ultrasound tip 11 is inserted into the vial 12 but the tip 11 does not come into contact with the solution in the vial 12.

FIG. 1 shows delivery of ultrasound energy where the ultrasound tip 3 is inserted into the vial 4 and into the solution—there are three different types of recommended methods for this direct sonication. FIG. 6 shows the first method that uses a special shaped vial where the ultrasound tip remains in the same position during the delivery of the ultrasound energy, while FIG. 7 shows the last two methods that utilize movement of the ultrasound tip during the sonication treatment.

FIG. 6 shows the first method of direct sonication that uses both a special shaped vial 26, 28, or 30 and a corresponding ultrasound tip 25, 27, or 29 that mirrors the shape of the vial 26, 28, or 30. There are three different recommended shapes of vials 26, 28, or 30 to use with a corresponding ultrasound tip 25, 27, or 29: the three shapes are FIG. 6a a spherical vial 26, FIG. 6b a rectangular vial 28, and FIG. 6c a curved vial 30. With the spherical vial 26 shown in FIG. 6a, a spherical shaped ultrasound tip 25 is inserted into the bottom of the vial 26. Because the ultrasound tip 25 mirrors the shape of the vial 26, there is an equidistant space between the ultrasound tip 25 and the vial 26; this allows for the solution to be sonicated equally, thus resulting in an effective vaccine creation. This same concept of equal sonication also applies to the rectangular shaped vial 28 shown in FIG. 6b. A rectangular-shaped ultrasound tip 27 that mirrors the shape of the vial 28 is inserted into the solution therefore causing the solution to be sonicated equally. Finally, the curved shaped ultrasound tip 29 shown in FIG. 6c can be inserted into a curved shaped vial 30, therefore allowing for equal sonication of the solution contained in the vial 30. The shapes of the vials 26, 28, or 30 contained in FIG. 6 are the recommend shapes, and the preferred shape is the spherical vial 26; other similar shapes or combinations of shapes of vials and ultrasound tips can also be utilized.

FIG. 7 shows the second potential method of direct sonication where the ultrasound tip 31 is inserted into the bottom of the vial 32 containing the solution and then the tip rises in a continuous motion 33 as it delivers ultrasonic energy. After the sonication begins, the ultrasound tip 31 gradually rises to the top of the solution while delivering ultrasound energy. The ultrasound tip 31 stops its movement and stops delivering ultrasound energy after it reaches the top and the entire solution has been sonicated. This movement during the delivery of ultrasound energy allows for equal sonication of the entire solution, which is effective because it ensures that the harmful cells and viruses are destroyed to prevent toxicity and that the antigens are released. This is more effective than inserting the tip to the bottom of a regular shaped vial and attempting to sonicate the entire solution from one position—delivering from one position results in varying sonication because the distance of the solution to the ultrasound tip varies throughout the vial.

FIG. 7 also shows the third potential method of direct sonication where the ultrasound tip 31 is inserted into the bottom of the vial 32 containing solution and the tip 31 rises in a step-mode motion 34. Sonication occurs for a brief time and then stops. The ultrasound tip 31 is moved slightly higher, and then sonication occurs again. This step-delivery motion 34 is repeated until the tip 31 has moved to the top and the entire solution has been sonicated. Similarly to the continuous movement delivery, this method allows for equal sonication of the entire solution. This distance between delivery steps in this step-mode delivery method can be of equal or varying distances.

FIG. 8 shows a cross-sectional view of a production-line sonication method to use with the ultrasound vaccine development system. Vials 38 move down the production line towards the ultrasound tip 35. Upon reaching the tip 35, the tip 35 moves down 37 into the vial 36 to sonicate the solution contained in the vial 36. After sonication the ultrasound tip 35, moves back up 37 and waits until another vial 38 moves to the ultrasound tip 37. This process is repeated to sonicate multiple vials 38. There are multiple options in which the solution can be inserted in the vials 38. Pre-filled vials 38 can be placed on the line, the ultrasound tip 37 can fill the vial 36 with the solution through a central orifice (not shown) in the ultrasound tip 37, or there can be a separate delivery mechanism/source or sources (not shown) that can fill the vials 38 as they move down the production line and towards the ultrasound tip 35. There are also multiple versions of the system that can be used—besides using different methods of filling the vials with solution, one or more ultrasound tips can deliver ultrasonic energy to one or more vials at a time. Furthermore, different methods of direct sonication where the ultrasound tip is inserted solution can also be used as described above.

FIG. 9 is a cross-sectional view of a carousel sonication method to use with the ultrasound vaccine development system. Vials 42 are placed in the carousel system and rotate around the carousel until they reach the ultrasound tip 39. When the vial 40 reaches the ultrasound tip 39, the tip 39 moves down 41 into the vial 40 to sonicate the solution contained in the vial 40. After sonication, the ultrasound tip 39, moves back up 41 and waits until another vial 42 moves to the ultrasound tip 39. This process is repeated to sonicate multiple vials 42. There are multiple options in which the solution can be inserted in the vials 38. Pre-filled vials 42 can be placed in the carousel, the ultrasound tip 39 can fill the vial 40 with the solution through a central orifice (not shown) in the ultrasound tip 39, or there can be a separate delivery mechanism/source or sources (not shown) that can fill the vials 42 as they rotate around the carousel and towards the ultrasound tip 39. Furthermore, different methods of direct sonication where the ultrasound tip is inserted solution can also be used as described above. The production line method and the carousel method are only recommended systems to sonicate vials of solution. Additional methods and systems can be similarly effective.

Based on the ultrasound intensity that is utilized, the sonication time of the solution can be from fractions of a second and above for both pulse and continuous wave mode delivery. However, the intensity of the ultrasound waves can be controlled through a variation in the ultrasound parameters such as the frequency, the amplitude and the treatment time. The recommended frequency range for the ultrasound waves is 16 kHz to 20 MHz, with the preferred frequency range of 30 kHz to 120 kHz, and the most preferred frequency value is 50 kHz. The amplitude of the ultrasound waves can be 2 microns and above, with the recommended amplitude to be in range of 3 microns to 250 microns, and the most preferred amplitude value is 80 microns. The recommended sonication treatment time is 5-10 seconds. The amount of solution in the vial is at least 0.1 grams, and the preferred amount of solution is 5-10 grams.

The process may require different intensity levels and ultrasound parameters based on the specific type of virus, bacterium or other infectious agent used to create the vaccine and based on the amount of the solution to be sonicated. For example, 5 ml of a solution can be sonicated with an ultrasound frequency of 50 kHz, an amplitude of peak to peak 50 microns, an intensity of about 1000 watts/cm$^2$, and the sonication time will take up to 10 seconds based on the type of virus, bacterium, etc solution. The longer the sonication time of the solution, the lower the level of intensity is required; the shorter the sonication time, the higher the level of intensity is required. The sonication of the solution can be conducted in different temperature environments, but the preferred method is to use room temperature.

Although specific embodiments and methods of use have been illustrated and described herein it will be appreciated by those of ordinary skill in the art that any arrangement that is calculated to achieve the same purpose may be substituted for the specific embodiments and methods shown. It is to be understood that the above description is intended to be illustrative and not restrictive. Combinations of the above embodiments and other embodiments as well as combinations of the above methods of use and other methods of use will be apparent to those having skill in the art upon review of the present disclosure. The scope of the present invention should be determined with reference to the appended claims, along with the full scope of equivalents to which such claims are entitled.

I claim:

1. A method for creating a vaccine by using ultrasound energy, comprising the steps of:
   providing a container for holding a solution containing an infectious agent;
   providing an ultrasound tip having a central orifice through which solution can flow;
   producing a sonicated solution by delivering a solution containing an infectious agent though the central orifice of the ultrasound tip into the container while emitting ultrasound waves from the ultrasound tip such that all portions of the solution receive approximately the same ultrasound dosage resulting in release of antigens from the infectious agent and degradation of the viability of the infectious agent;
   wherein the sonicated solution is a vaccine.

2. The method according to claim 1 wherein geometrical proportionality between the ultrasound tip and the container is maintained.

3. The method according to claim 1 wherein the ultrasound waves have an amplitude of at least 2 microns.

4. The method according to claim 1 wherein the ultrasound waves have an amplitude in the range of 2 microns to 250 microns.

5. The method according to claim 1 wherein the ultrasound waves have an amplitude of approximately 80 microns.

6. The method according to claim 1 wherein the ultrasound waves have a frequency in the range of 16 kHz-20 MHz.

7. The method according to claim 1 wherein the ultrasound waves have a frequency in the range of 30 kHz-120 kHz.

8. The method according to claim 1 wherein the ultrasound waves have a frequency of approximately 50 kHz.

9. The method according to claim 1 wherein the ultrasound waves are emitted intermittently for a duration of at least a fraction of a second.

10. The method according to claim 1 wherein the ultrasound waves are emitted for a duration in the range of 5-10 seconds.

11. The method according to claim 1 wherein the mass of said solution containing an infectious agent is at least 0.1 grams.

12. The method according to claim 1 wherein the mass of said solution containing an infectious agent is between 5 and 10 grams.

13. The method according to claim 1 wherein the shape of the ultrasound tip mirrors the shape of the container.

14. The method according to claim 1 wherein the step of producing the sonicated solution comprises delivering the ultrasonic waves from the ultrasound tip to the container through an air or gas medium.

15. The method according to claim 1 wherein the shape of the ultrasound tip mirrors the outside shape of the container in which the tip contacts so that the whole tip is in contact with the vial.

16. The method according to claim 1 wherein the vaccine is created from the solution containing an infectious agent without the use of a chemical.

17. The method according to claim 1 wherein the ultrasound tip is of a substantially spherical shape.

* * * * *